US011000856B2

(12) United States Patent
Pal et al.

(10) Patent No.: US 11,000,856 B2
(45) Date of Patent: May 11, 2021

(54) CANNABIS TRICHOME SEPARATION USING A TUMBLER

(71) Applicant: Nextleaf Solutions Ltd., Coquitlam (CA)

(72) Inventors: Krupal Devendra Pal, Burnaby (CA); Thomas Adam Ulanowski, Langley (CA); Ivan Jason Casselman, Vancouver (CA)

(73) Assignee: Nextleaf Solutions Ltd., Vancouver (CA)

( * ) Notice: Subject to any disclaimer, the term of this patent is extended or adjusted under 35 U.S.C. 154(b) by 266 days.

(21) Appl. No.: 16/413,424

(22) Filed: May 15, 2019

(65) Prior Publication Data

US 2020/0360930 A1 Nov. 19, 2020

(51) Int. Cl.

| | |
|---|---|
| ***B02C 21/00*** | (2006.01) |
| ***B02C 23/14*** | (2006.01) |
| ***B02C 23/10*** | (2006.01) |
| ***B02C 23/16*** | (2006.01) |
| ***B07B 1/36*** | (2006.01) |

(52) U.S. Cl.
CPC .............. *B02C 21/00* (2013.01); *B02C 23/10* (2013.01); *B02C 23/14* (2013.01); *B02C 23/16* (2013.01); *B07B 1/36* (2013.01); *B02C 2023/165* (2013.01)

(58) Field of Classification Search
CPC ......... B02C 21/00; B02C 23/06; B02C 23/14; B02C 23/38; B02C 19/186; B01D 11/028; B01D 11/0292; B01D 29/56; B01D 37/00
USPC ........................................................... 241/37
See application file for complete search history.

(56) References Cited

U.S. PATENT DOCUMENTS

| | | | | |
|---|---|---|---|---|
| 9,532,593 | B2 * | 1/2017 | Turner | A24B 15/16 |
| 10,172,897 | B2 * | 1/2019 | Vu | A61K 36/185 |
| 10,780,442 | B2 * | 9/2020 | Pal | A24B 15/00 |
| 2017/0001200 | A1 * | 1/2017 | Leffel | B02C 23/10 |
| 2017/0188623 | A1 * | 7/2017 | Cranford | A61K 31/352 |
| 2018/0339298 | A1 * | 11/2018 | Mayers | G01G 17/02 |
| 2018/0352848 | A1 * | 12/2018 | Vu | A24D 1/18 |
| 2019/0168232 | A1 * | 6/2019 | Bruggemann | B02C 17/1855 |
| 2020/0108018 | A1 * | 4/2020 | Shadurin | A24D 1/02 |
| 2020/0191480 | A1 * | 6/2020 | Baughman | F26B 5/06 |
| 2020/0308133 | A1 * | 10/2020 | Stephens | B01D 21/0012 |

* cited by examiner

*Primary Examiner* — Faye Francis
(74) *Attorney, Agent, or Firm* — Damien G. Loveland

(57) ABSTRACT

Raw *cannabis* plant material is dried, coarsely ground, agitated while chilled, sifted and collected to result in *cannabis* plant material rich in trichomes. Dried *cannabis* plant material is coarsely ground using a grinder. The coarsely ground *cannabis* plant matter is agitated in a tumbler in a cooled environment to separate the trichomes from the remainder of the plant matter. The trichomes are then sieved using a sieve shaker with sieves of different mesh sizes mounted in a tower. Chilling the plant material embrittles the trichomes so that they can be removed more easily from the remainder of the plant material.

14 Claims, 1 Drawing Sheet

CANNABIS TRICHOME SEPARATION USING A TUMBLER

TECHNICAL FIELD

This invention relates to a method for refining raw *cannabis* plant material. More specifically, it relates to a method for separating cannabinoid-rich trichomes from raw *cannabis* plant material using a tumbler, a cooler and sieving techniques.

BACKGROUND

In legal, adult-use markets, sales of *cannabis* extracts are growing ten times faster compared to the sales of dried *cannabis*, and extracts account for over 60% of revenue. With *cannabis* legalization, consumer preferences are shifting from dried *cannabis* to extracted *cannabis* products. Thus, the development of new, scalable refinement and extraction techniques in order to propose products with fewer impurities to the consumers, different flavors or new ways of consumption, is important for the *cannabis* industry.

Most psychoactive substances are contained in parts of the *cannabis* plant that are called trichomes, which can be defined as epidermal outgrowths of the plant. It is usually necessary to separate these trichomes from the raw *cannabis* plant material to produce *cannabis*-based products.

This background is not intended, nor should be construed, to constitute prior art against the present invention.

SUMMARY OF INVENTION

*Cannabis* products are created in such a way that a high content of cannabinoids and terpenoids in these products is achieved. Thus, isolating trichomes from the raw *cannabis* plant material before running any extraction process helps to improve the quality of downstream *cannabis* products and can be considered to be an initial refinement step in processes that further refine the separated trichomes. In some cases, refinement may be defined as the division of separated trichomes into fractions of different sizes.

Beside this, there are various forms of trichome in the *cannabis* plant. Each type has a certain size and/or cannabinoid and terpenoid content and therefore will exhibit various purity grades. For example, the trichomes contained in the head of the *cannabis* plant have a higher concentration of phytomolecules compared to the ones found on the stalk. Therefore, the separation of these different forms of trichome is important for choosing the best starting material for a further extraction process, if any, and to obtain cannabinoid products with a high cannabinoid content, such as cannabidiol (CBD) or delta-9-tetrahydrocannabinol (THC). *Cannabis* plants grow THCA (delta-9-tetrahydrocannabinolic acid) and CBDA (cannabidiolic acid) and, over time, due to temperature, these "acidic" molecules slowly convert to their neutral THC or CBD forms, which are then much more active. However, this conversion can be accelerated in a specific decarboxylation step.

The present invention is a two-stage separation process that aims to separate trichomes from raw *cannabis* plant material or biomass using a tumbler, a cooler and a sieve shaker. The raw *cannabis* plant material is first dried, coarsely ground, chilled, then placed in a tumbler, which is also chilled. The chilled, coarsely ground *cannabis* plant material is then tumbled, which causes the trichomes to separate from the plant matter. The trichomes fall through the mesh of the tumbler and are separated by means of a sieve shaker into various size fractions. Finally, every fraction of the sifted *cannabis* plant material is collected and stored in a dry, dark, cold room.

Disclosed here is a process for separating trichomes from raw *cannabis* plant material comprising the steps of: drying the raw *cannabis* plant material to result in dried *cannabis* plant material; coarsely grinding the dried *cannabis* plant material using a grinder with a mesh size between 1.0 cm (3/8 in) and 2.5 cm (1 in) to result in coarsely ground *cannabis* plant material; agitating the coarsely ground *cannabis* plant material in a tumbler at a temperature between 5° C. and −40° C. to result in separation of trichomes from the coarsely ground *cannabis* plant material; collecting the trichomes that fall through a mesh that forms a wall of the tumbler; and sieving the collected trichomes to form fractions of trichomes of different sizes.

BRIEF DESCRIPTION OF DRAWINGS

The following drawings illustrate embodiments of the invention, which should not be construed as restricting the scope of the invention in any way.

DESCRIPTION

A. Glossary

Trichomes are fine outgrowths or appendages that can be found on the *cannabis* plant.

Cannabinoids are a group of chemicals that act on cannabinoid receptors in the body, numerous of which are found in the *cannabis* plant.

Terpenoids are naturally occurring organic chemicals derived from terpenes, most having multicyclic structures and oxygen-containing functional groups. Plant terpenoids are used for their aromatic qualities and play a role in traditional herbal remedies.

Phytomolecules are chemical compounds produced by plants, usually to help them thrive or to thwart competitors, predators, or pathogens. They may be used as traditional medicine.

Tetrahydrocannabinol (THC) refers to a phytocannabinoid molecule that is found in only small amounts in *cannabis* plants and is known for its psychoactive effect when consumed or inhaled. It is more correctly known as delta-9-tetrahydrocannabinol.

Tetrahydrocannabinolic acid (THCA) is a non-psychoactive cannabinoid found in *cannabis*. THCA is the acidic form and precursor to THC. THCA converts to THC via decarboxylation when exposed to heat or sunlight.

Cannabidiol (CBD) refers to a phytocannabinoid molecule that is obtained, after heating, from the CBDA found in *cannabis* plants.

Cannabidiolic acid (CBDA) is a non-psychoactive cannabinoid and the acidic precursor to CBD, and can be found in *cannabis* plants. CBDA converts to CBD through decarboxylation, which occurs when *cannabis* is exposed to heat or sunlight.

"Separation", in relation to tumbling, refers to the detachment of trichomes from other *cannabis* plant material. In relation to sieving, "separation" refers to the division of the trichomes into different size fractions.

B. Exemplary Process

Figure 1:
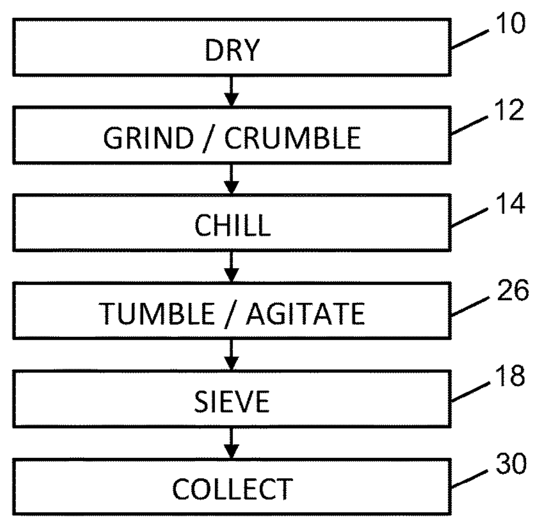
FIG. 1 is a high-level flowchart describing the key steps for separating the trichomes from the raw *cannabis* plant material according to an embodiment of the present invention.

Referring to FIG. 1 there is shown in more detail the steps of the process used to separate the trichomes from the raw *cannabis* plant material. In a first step 10, the raw *cannabis* plant material is dried with a temperature set between 15° C. and 40° C. The raw *cannabis* plant material should be dried in order to maximize the efficiency of the later coarse grinding and separation processes. Ideally, after the drying step 10, the moisture content (understood as percentage by weight herein) in the dried *cannabis* plant material should be 6-12%. However, a preferred moisture content is 6-10%. A moisture content of over 12% in the dried *cannabis* plant material increases potential for microbial growth, which can be responsible for product degradation, and so keeping the moisture content below 10% ensures long-term product stability. A high moisture content also has the tendency to make the plant matter 'wet' while sieving and or during the coarse grinding process.

At the same time, a moisture content below 6% in the *cannabis* plant material is not worth achieving since the material will absorb moisture when exposed to ambient air.

In some embodiments, after the drying step 10, the dried *cannabis* plant material is introduced into a grinder with a mesh size that is between 1 cm (⅜ in) and 2.5 cm (1 in) and ground in step 12. The grinder coarsely grinds or crumbles the dried *cannabis* plant material, and may be considered to be partial grinding. This coarse grinding is conducted in such a manner that parts of the dried *cannabis* plant material are reduced to an optimized size for the subsequent tumbling process. The size of the grinder mesh and hence the coarsely ground *cannabis* plant material should be kept large enough to avoid the separation of the trichomes from the plant material during the coarse grinding step. Indeed, the trichomes should not be finely ground, and neither should the other *cannabis* plant material, as the sieving stage would then contain undesired ground *cannabis* plant matter along with trichomes reducing the product quality, which would lead to lower product purity, and in some cases a lower yield. A finely-ground trichome will be difficult to separate from the rest of the finely-ground *cannabis* plant material. The coarse grinding process helps to gently and safely break up the voluminous portions of the *cannabis* plant, exposing more surface area, and facilitating the later separation of the trichomes from the remainder of the coarsely ground *cannabis* plant material.

After coarse grinding, the dried *cannabis* plant material is chilled in a cold room or cold chamber in step 14. The temperature in the cooling room or chamber is set between 5 and −40° C.

In step 18, the cooled, coarsely ground *cannabis* plant material (i.e. coarsely ground biomass) is placed in a tumbler in the cold room or a cooling chamber in order to facilitate the separation of the trichomes from other parts of the coarsely ground *cannabis* plant material. In relation to the tumbler and the action of tumbling, "separation" refers to the detachment of the trichomes from the *cannabis* plant material. The tumbler serves as an initial or 'pre-separation stage', separating trichomes from the rest of the plant matter by the tumbling process. Steps 14 and 18 may be carried out simultaneously.

*Cannabis* plant material is usually collected in the form of *cannabis* buds. The *cannabis* buds have trichomes inside their core structure, while leaves are located in the outer part of the buds. The three-dimensional nature of the leaves prevents the trichomes from being knocked off. The tumbler is used mostly for separation purposes. However, the rotating action of the tumbler may break trichomes and other plant matter. The chilled trichomes are brittle and they tend to break away from the plant matter upon rotation. In some instances, only leaves are present. In other cases, other *cannabis* can be put in unmanicured. The mechanical agitation of the tumbling process causes the separation of trichomes from the rest of the plant material, prior to the sieving of the trichomes. Tumbling the *cannabis* plant material thus increases the purity grade of the material that is subjected to the sieving procedure.

For the tumbling step 18, in which the coarsely ground *cannabis* plant matter is agitated, the speed of rotation applied to the tumbler is slow in order to gently separate all or a majority of the trichomes from the buds, leaves and stems, and to gently break the buds and plant matter, if at all. If the speed of rotation is too high, the plant material other than trichomes will break into smaller parts and therefore will be difficult to separate from the trichomes. Also, while unlikely, some of the trichomes may be broken up. The risk of not properly separating the trichomes from the plant material may be problematic, which will lead to a final product with a lower purity grade and/or overall lower yield.

The inner surface of the tumbler is porous with a mesh size of 250 μm in order to separate the trichomes from the larger parts of the coarsely ground *cannabis* plant material.

The tumbling step 18 is conducted in a cold environment by operating the tumbler in a cold room or in a cold chamber. The temperature during step 18 is set between 5° C. and −40° C. The cold temperature allows for the trichomes to become more brittle, which eases the separation process during tumbling. When the temperature of the dried *cannabis* plant material is above 5° C., the brittleness of the trichomes starts to decrease. Therefore, the temperature of the dried *cannabis* plant material during any mechanical separation process should be maintained below 5° C. in order for the process to be efficient. The chilling step 14 and chilled tumbling step 18 are conducted under standard atmospheric pressure, since pressure does not have any significant effect on both the breakage efficiency and the subsequent separation of the trichomes from the coarsely ground *cannabis* plant material.

For example, a temperature of −20° C. is used to run the tumbling step 18. The duration of the tumbling step is also dependent on the temperature at which the tumbling takes place, and is typically in the range of 2-60 minutes. Tumbling continues until there is relatively little material passing through the tumbler screen, or there is a physical change to the material passing through. If the agitation during tumbling is sufficient, then the raw *cannabis* material can be considered to be spent. If the agitation is not sufficient, then the tumbled *cannabis* can be tumbled again. When the temperature is cooler, less time is needed for tumbling as the *cannabis* plant material as a whole is more brittle than when the temperature is warmer.

When tumbling occurs between 0° C. and 5° C., the percentage trichome content in the plant matter obtained from the tumbler will be higher than for a temperature range of 0° C. to −40° C. When the temperature is over 0° C., the probability of breaking undesirable parts of the plant, such as leaves or stems, decreases. Therefore, a temperature above 0° C. is used when the lack of contamination in the product, due to plant matter other than trichomes, is more important than the overall yield.

For a temperature below 0° C., the trichomes are more brittle, which means that more of them are broken away from the remainder of the plant material, and more of them are broken up. As a consequence, more trichomes are extracted, as more will pass through the first sieve. This will increase the yield of the process. If the process is run between 0° C. and −20° C., the purity will be higher and the yield will be lower than if the process were run at a temperature range between −20° C. and −40° C. This is because between −20° C. and −40° C., the plant material overall is more brittle than between 0° C. and −20° C., and more of it breaks up. Depending on the relative importance of yield and purity, different temperature ranges may therefore be selected to optimize the process.

However, for a temperature below −40° C., every part of the *cannabis* plant material including trichomes starts to break up into smaller parts. As a result, the sieving process will result in products that are difficult to separate from each other through their size. Thus, the separation of the trichomes from other parts of the *cannabis* plant material is no longer effective.

The *cannabis* plant material that has passed through a screen or mesh wall of the tumbler is then placed onto a top sieve of a sieve shaker in step 26. The sieve shaker is arranged in a tower setup style and contains a series of three sieves mounted on an agitation module. The top sieve in the sieve shaker has a pore size of 200-212 μm mounted on a middle sieve with a pore size of 149-177 μm. This middle sieve is mounted on a bottom sieve of pore size 63-75 μm, which is mounted on the agitation module. The coarse particles are retained by the top sieve while the finest particles pass through one or more of the three sieves. Usually, the *cannabis* plant material that falls through all the sieves represents the most potent fraction of the separation process, i.e. the *cannabis* plant material that has the highest content in trichomes. The three stage sieve shaker is used to separate the trichomes based on size. In relation to sieving, “separation” is used to refer to the division of the trichomes into different size fractions. There are different forms of trichome in the *cannabis* plant material that can be characterized via their size. Indeed, different types of trichome with different sizes can be found in the stalk or the head of the *cannabis* plant. The aim of the separation process based on the size of the trichome is to achieve different purity grades related to each collected fraction. The most potent output materials are obtained when using a sieve size range of 60-100 μm. The smaller the sieve size is, the more potent is the collected fraction, since only the smaller part of the trichome (i.e. the head of the trichome where the majority of the cannabinoids and terpenoids are retained) is preferentially collected.

The speed of agitation during the sieving step 26 has to be selected properly in order to avoid the contamination of the target trichomes. When the speed of agitation in the sieve shaker is too high, the non-trichome plant materials, such as pistils or small bits of leaves, are more prone to break into smaller parts. This can cause contamination, since the separation of the trichomes from the smaller parts of the *cannabis* plant material is more difficult to achieve. Likewise, care should be taken not to extend the duration of the sieving so much as to start to break up any of the non-trichome plant material into small parts that would pass through one or more of the sieves.

The sieve shaker is run for 2-7 min or until the fine parts of the chilled *cannabis* plant material have passed through the top sieve. The separation process takes place by inducing vibration of the plant material. The amplitude of the vibration can be altered based on the separation process. While chilling is not required, the sieve shaker may be operated in a cold room or an environment where the temperature can be controlled. Ideally, the temperature of the sieve shaker should be maintained below 20° C. Colder temperatures may be implemented for better separation results and to maintain quality, and to prevent “gumming” up of the sieves. Temperatures between 1° C. and 20° C. are typically used to run the sieve shaker for the trichome separation.

The sieving step 26 is run in an environment with a relative humidity below or at 60%. The lower the humidity is, the better for the efficiency of the sieving step 26. The sieving step can also be run at atmospheric conditions.

The sieved *cannabis* plant material is then collected in individual fractions in step 30 and stored in a cold dark room in order to be preserved from degradation. When the trichomes are exposed to light, particularly if the light contains high-energy UV wavelengths, for an extended period of the time, degradation of the active ingredients contained in the trichomes may occur. The storage conditions are those that are usually used in the pharmaceutical industry to store active pharmaceutical ingredients. Colder temperature storage environments reduce the rate of decomposition of the active ingredients. For example, cannabinoids and terpenes stored in a freezer at −20° C. or in a refrigerator at 4° C. will not degrade significantly over a period of 6 to 12 months. Cold storage temperatures also help to prevent microbial activity such as molds or bacteria from growing. An optimal storage environment for preserving the active ingredients present in the trichomes would be a dark, dry and cold environment. However, if the trichomes have to be used the day after their collection, the trichomes can be stored at room temperature as they will not be prone to significant degradation by exposure to ambient light and temperatures for such a short period of time.

Optionally, the trichome content of each fraction of sifted *cannabis* plant material may be measured to determine the yields of the separation process. Generally, the yield depends on the quality of the raw *cannabis* plant material input, and separation efficiency during the agitation step performed within the tumbler. Some *cannabis* plants possess more trichomes than others. The typical observed yield is about 10% by weight of the raw *cannabis* plant material.

C. Exemplary Apparatus

Figure 2:
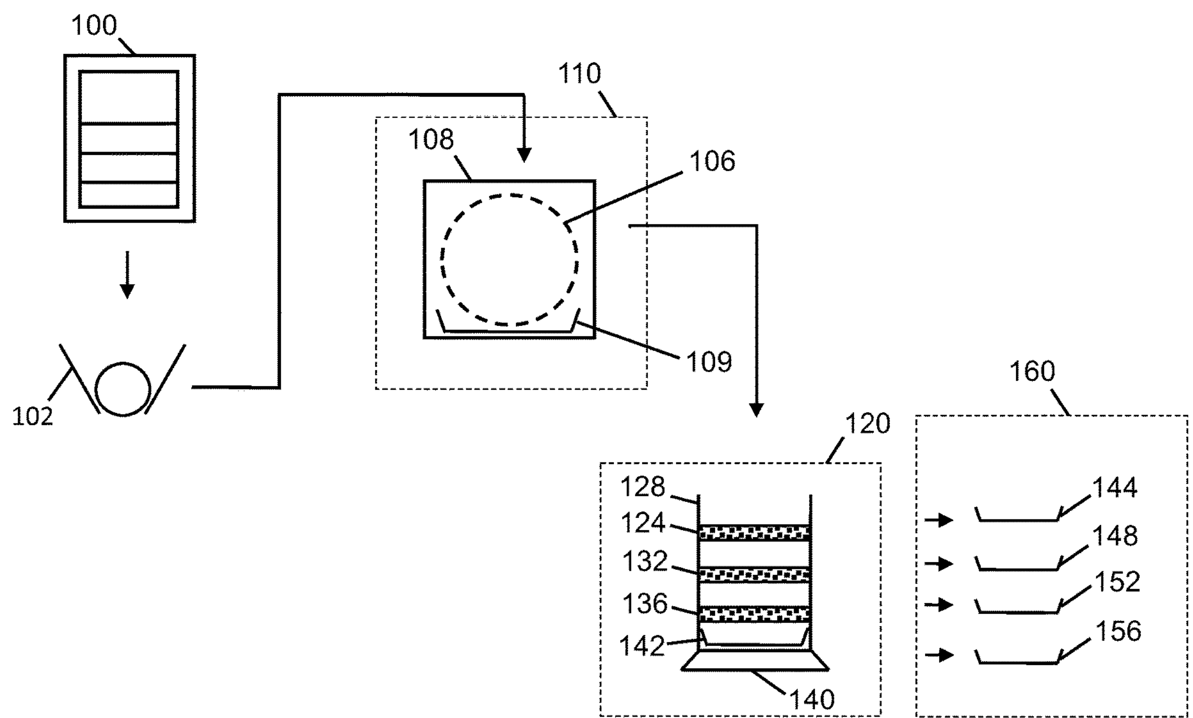
FIG. 2 is a schematic diagram of the apparatus used to separate the trichomes from the raw *cannabis* plant material according to an embodiment of the present invention.

Referring to FIG. 2, an oven 100 may be used to dry the raw *cannabis* plant material. The raw *cannabis* plant material is positioned on a tray or a flat surface inside the oven 100.

Then, the dried *cannabis* plant material is coarsely ground. The coarse grinding is achieved using a grinder 102 with a mesh size that is between 1 cm (⅜ in) and 2.5 cm (1 in). The coarse grinding is complete or partial and conducted in such a manner that parts of the dried *cannabis* plant material are reduced to a size that improves the efficiency of the tumbling step. Coarse grinding occurs at room temperature in order to reduce premature breaking away of the trichomes.

After that, the dried, coarse grinding *cannabis* plant material is loaded into a tumbler 108. In some embodiments, this tumbler is located in a cold environment 110. The mesh size of the tumbler, if present, is 250 μm, and the trichomes that are separated from the remainder of the plant material fall through the mesh 106 into tray 109. However, the tray 109 may be eliminated if the tumbler is arranged so that the trichomes fall directly onto the top sieve 124. This latter arrangement may make the process more continuous and scalable.

The tumbler is rotated in order to agitate the coarsely ground, dried, *cannabis* plant material and separate the trichomes from the coarsely ground, dried *cannabis* plant material. The speed of the rotation should be sufficiently high to continually lift a sizeable fraction of the coarsely ground, dried *cannabis* plant material so that it falls onto the remainder of the coarsely ground, dried *cannabis* plant material in the tumbler. The action of plant material falling onto other portions of the plant material results in the agitation of the plant material leading to separation of the trichomes from the rest of the plant material. The rotations per minute (rpm) of the tumbler vary depending on the diameter of the drums. For example, for a drum of 0.5 m diameter, the speed of the rotation should be around 60 rpm. For a drum of 3 m, the speed of the rotation is around 25 rpm. As the drum diameter increases, the speed of the rotation decreases to maintain a satisfactory trichome separation without undue breakage of the remainder of the plant material into parts that are of similar size to the trichomes.

The chilled *cannabis* plant material is then placed on a top sieve 124 of a sieve shaker 128. The sieve shaker 128 is a series of three sieves (top sieve 124, middle sieve 132 and bottom sieve 136) mounted on an agitation device 140. The sieve shaker 128 is optionally in a cold environment 120. In some embodiments, the sieve shaker 140 is placed in an environment at room temperature. The top sieve 124 has a pore size of 200-212 μm. The middle sieve 132 has a pore size of 149-177 μm. The bottom sieve 136 has a pore size of 63-75 μm. Below the bottom sieve 136 there is a collection tray 142. The sieve shaker 128 with the *cannabis* plant material is run for 2-7 min, or until all of the plant material has been sieved. This could be 3 hours, depending on size of sieve, vibration strength, and amount of trichomes, etc. After that, the chilled *cannabis* plant material retained on the top sieve 124 is transferred to a tray 144 in order to be stored in a cool, dry, dark room 160. The fractions of sifted *cannabis* plant material retained by the middle 132 and bottom sieves 136 are respectively transferred to the trays 148 and 152 in order to be stored in the cool, dry, dark place 160. The sifted *cannabis* plant material that has passed through all the sieves 124, 132, 136 is collected on a tray 142 and transferred to tray 156 in order to be also placed in the cool, dry, dark room 160. In some embodiments, only the tumbler 108 is placed in a cold environment 110 while the sieve shaker 128 is at room temperature.

D. Variations

The entire process can be carried out at room temperatures, eliminating the chilling aspect. However, the quality and yield of the product will be affected.

The coarse grinding step can be removed, but yield and product quality will be affected.

A tumbler with a rotating shaft may be used to implement coarse grinding as well as separation of trichomes from the plant matter at the same time, due to the rotational motion of the tumbler.

In some embodiments, fresh raw *cannabis* plant material can be ground directly without being previously dried. Preferably, however, the raw *cannabis* plant material is dry.

In some embodiments, the tumbler does not have a mesh and the entire contents of the tumbler after coarse grinding, and potentially some separation of the trichomes, are placed onto the top sieve of the sieve shaker directly.

In some embodiments, the tumbler has nodules on its inner surface that are pointing toward the inner volume of the tumbler in order to facilitate the separation of the trichomes from the buds. These nodules are rounded but can alternately be sharp to facilitate the shredding of the buds. In some embodiments, a tumbler with sharp nodules is used instead of the grinding step.

Various other numbers of sieves in the sieve shaker with different mesh sizes may be used. The number of sieves is determined by the goal of the extractor. If purity is not important, but overall yield is, one sieve would be used, or none, since the tumbler is the primary sieve. The selection of the sieves can be made based on the desired product. For example, only a 250 μm sieve will be used if that size corresponds to the product of interest. If different "grades" or "purities" are required, a larger number of sieves would be used.

Typically, the goal is to remove as much trichome material as possible, without breaking up and concentrating leaf/plant tissue during the process. The yield depends on input materials; some *cannabis* has a lot of trichomes, and some has very little. The amount of trichomes varies in *cannabis*, depending on the quality of the plant matter. One typically aims for about 10% of the weight of the input raw *cannabis* plant material, but this is a very rough estimate.

In addition to or in place of the oven, a room outfitted with an HVAC (heating, ventilation and air conditioning) and dehumidification system could be used. In fact, this would be the case for a larger-scale system.

Temperatures that have been given to the nearest degree include all temperatures within a range of ±0.5° C. of the given value.

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. All parameters, dimensions, materials, and configurations described herein are examples only and may be changed depending on the specific embodiment. Accordingly, the scope of the invention is to be construed in accordance with the substance defined by the following claims.

The invention claimed is:

1. A process for separating trichomes from raw *cannabis* plant material comprising the steps of:

drying the raw *cannabis* plant material to result in dried *cannabis* plant material;

coarsely grinding the dried *cannabis* plant material using a grinder with a mesh size between 1.0 cm (⅜ in) and 2.5 cm (1 in) to result in coarsely ground *cannabis* plant material;

agitating the coarsely ground *cannabis* plant material in a tumbler at a temperature between 5° C. and −40° C. to result in separation of trichomes from the coarsely ground *cannabis* plant material;

collecting the trichomes that fall through a mesh that forms a wall of the tumbler; and sieving the collected trichomes to form fractions of trichomes of different sizes.

2. The process of claim 1, wherein drying the raw *cannabis* plant material is carried out at a temperature between 15° C. and 40° C.

3. The process of claim 1, wherein the dried *cannabis* plant material has a moisture content between 6% and 10%.

4. The process of claim 1, wherein the tumbler has nodules on its inner surface.

5. The process of claim 1, wherein the mesh has a size of 250 μm.

6. The process of claim 1, wherein the sieving comprises sieving the collected trichomes, in order, through:

a sieve with a pore size of 212-250 μm;

a sieve with a pore size of 149-177 μm; and a sieve with a pore size of 63-75 μm.

7. The process of claim 6, comprising shaking the sieves on a sieve shaker.

8. The process of claim 1, wherein the sieving occurs at a temperature between 1° C. and 20° C.

9. The process of claim 1, wherein the agitating occurs at a temperature between 0° C. and 5° C.

10. The process of claim 1, wherein the agitating occurs at a temperature between −20° C. and 0° C.

11. The process of claim 1, wherein the agitating occurs at a temperature between −40° C. and −20° C.

12. The process of claim 1, wherein the agitating occurs for a duration of 2 to 60 minutes.

13. The process of claim 1, wherein the sieving occurs for a duration of 2 to 7 minutes.

14. The process of claim 1, comprising rotating the tumbler at a speed of 25 to 60 revolutions per minute.

* * * * *